(12) United States Patent
Peters

(10) Patent No.: US 6,267,754 B1
(45) Date of Patent: Jul. 31, 2001

(54) COUPLINGS FOR MEDICAL CANNULAE

(76) Inventor: Joseph Lennox Peters, Highfield, Little Widbury Lane, Ware, Hertfordshire SG121 7AU (GB)

( * ) Notice: Subject to any disclaimer, the term of this patent is extended or adjusted under 35 U.S.C. 154(b) by 0 days.

(21) Appl. No.: 09/214,831
(22) PCT Filed: Jul. 16, 1997
(86) PCT No.: PCT/GB97/01936
  § 371 Date: Apr. 2, 1999
  § 102(e) Date: Apr. 2, 1999
(87) PCT Pub. No.: WO98/02206
  PCT Pub. Date: Jan. 22, 1998

(30) Foreign Application Priority Data

Jul. 17, 1996 (GB) .................................................. 9615010

(51) Int. Cl.[7] .................................................. A61M 25/00
(52) U.S. Cl. .................................................. 604/533; 604/905
(58) Field of Search .................................................. 604/905, 249, 604/250, 247, 533–539, 86, 88, 411, 412, 424

(56) References Cited

U.S. PATENT DOCUMENTS

| 4,340,052 | * | 7/1982 | Dennehey et al. | 604/905 |
| 4,405,312 | * | 9/1983 | Gross et al. | 604/905 |
| 4,473,369 | * | 9/1984 | Lueders et al. | 604/905 |
| 5,037,405 | * | 8/1991 | Crosby | 604/905 |
| 5,531,695 | * | 7/1996 | Swisher | 604/111 |
| 5,545,152 | * | 8/1996 | Funderburk et al. | 604/905 |

* cited by examiner

Primary Examiner—Manuel Mendez
(74) Attorney, Agent, or Firm—Dykema Gossett PLLC

(57) ABSTRACT

A medical coupling for a cannula or the like includes a female member (1) with a body providing a hub (4) defining a socket (11), a valve section (5) with a valve actuator (15) slidable on the body, and a finger gripping section, and a male member (2) including a spigot (20) for engagement in the socket (11), a cap (21) with a screw thread for engagement with a flange (9) of the hub (4), an internally splined sleeve (24) and a finger gripping section (22). When the spigot (20) is inserted into the socket (11), the cap (21) is rotated onto the flange (10) to hold them against being pulled apart, and the valve actuator is displaced to open the valve and to bring a splined collar (19) into locking engagement with the sleeve (24). A separate casing (30) is provided to form sealed housing around the coupled parts of the male and female members between their griping sections (6, 22).

20 Claims, 3 Drawing Sheets

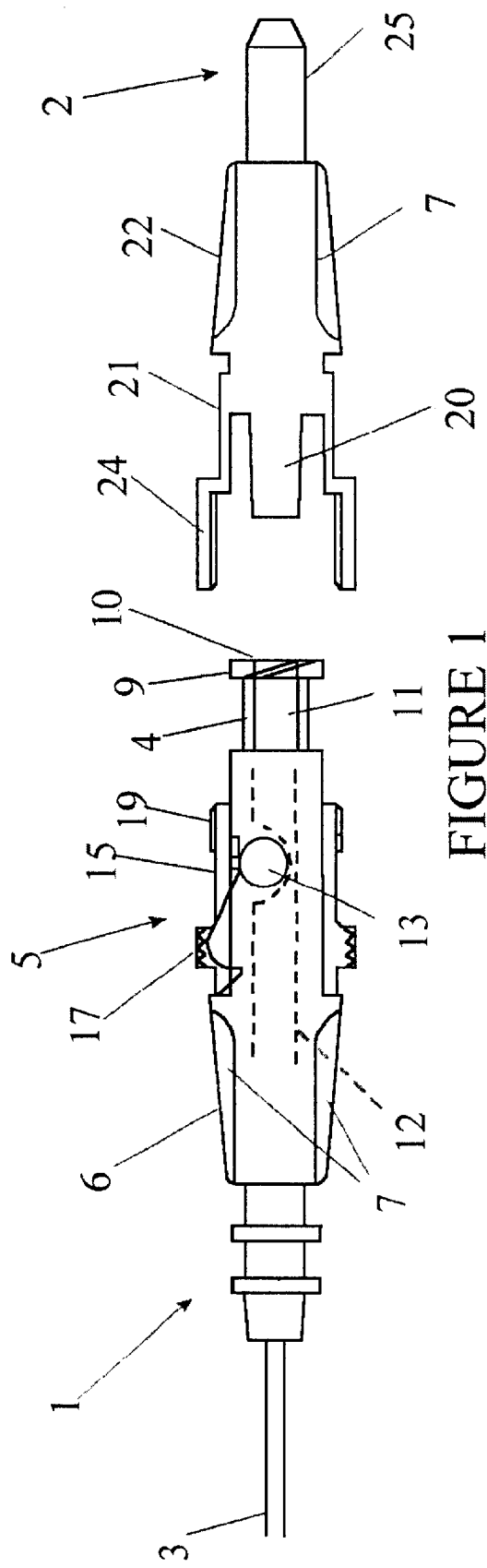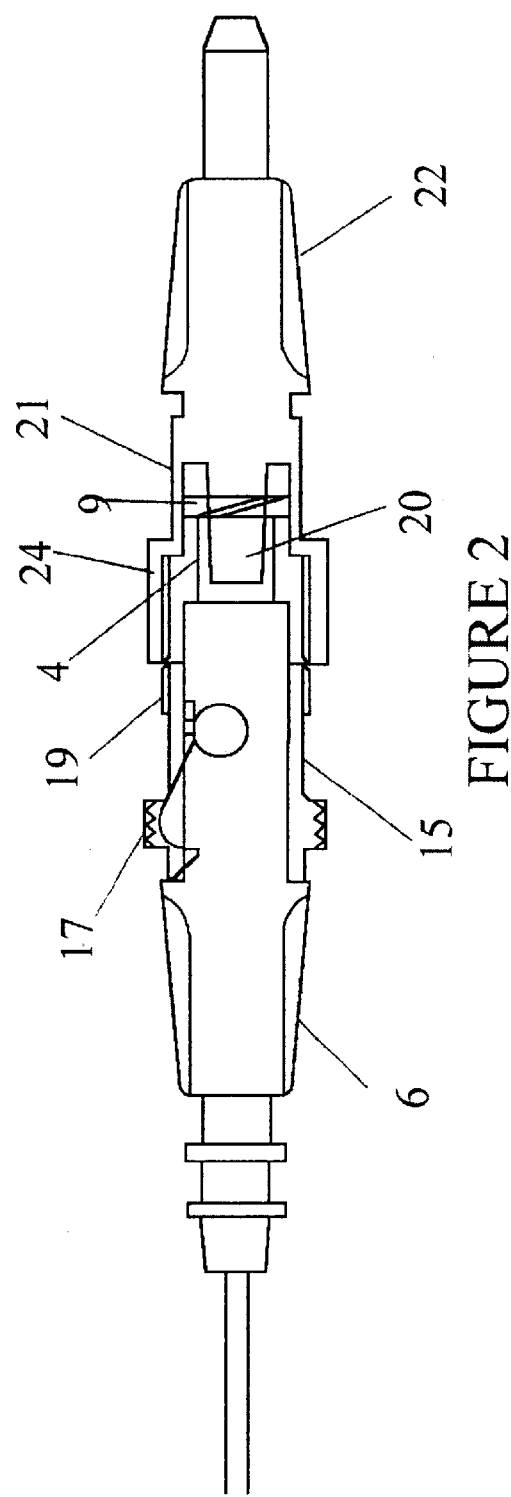
FIGURE 1
FIGURE 2

COUPLINGS FOR MEDICAL CANNULAE

BACKGROUND OF THE INVENTION

1. Field of the Invention

This invention is concerned with medical catheters and cannulae, and in particular is concerned with a coupling device for connecting a cannula or catheter to a connection tube through which liquid to be administered to a patient is delivered or fluid to be taken from a patient is collected.

2. The Prior Art

A form of coupling which has been in widespread use for many years comprises a female member fixed to the catheter end and having a moulded plastic hub defining an inwardly tapering frustoconical socket, and a male member which is fitted to the end of a connection tube forming part of an administration set for example, and which includes a tapering frustoconical spigot of complementary form to the hub socket for engaging therein with a friction fit. The coupling is made by pushing the male and female members together and is disconnected by pulling them apart. In order to help prevent unintentional disconnection it is known to equip the male member with an internally threaded cap which can be screwed onto a flange provided at the free end of the hub of the female member.

In WO 95/22369 there are described several improvements to medical cannulae couplings aimed at overcoming drawbacks inherent in the known coupling described above, especially regarding the dangers of air embolism should the coupling become unintentionally disconnected, and infection due to bacterial colonisation of the coupling. With the same basic objectives in mind the present invention is concerned with further improvements to medical cannulae couplings.

SUMMARY OF THE INVENTION

In accordance with one aspect the invention there is provided a coupling for a medical cannula or the like including a female member having a socket, a male member having a spigot engagable with a push fit into the socket, a cap attached to one member and rotationally engagable with the other member to secure the spigot against disengagement from the socket, and a locking arrangement to lock the cap against rotation in the direction of disengagement from the other member, characterised in that the locking arrangement includes a sleeve provided on the cap and a slide movable on the other member to engage the sleeve and thereby lock the sleeve and cap against rotation in the disengagement direction.

The coupling of the invention includes a novel system for locking the male and female members against accidental separation. Conveniently, the cap is provided on the male member and has a splined sleeve, and an axially movable slide on the female member is arranged to be engageable with the sleeve to lock the sleeve, and hence the cap, against rotation relative to, the hub of the female member.

Conveniently, the sleeve is internally splined and the slide includes a collar with external splines of complementary configuration and arrangement to the sleeve splines. To facilitate locking engagement of the collar with the sleeve after the cap has been tightened to secure the hub and spigot connection, the collar is preferably capable of limited rotational movement. e.g. through 10°–15°, to enable alignment between the splines of the sleeve and collar. The ends of the splines of the collar and/or sleeve can be shaped to guide the splines of the two parts into correct rotational alignment as the collar is moved from an unlocked to a locked position.

In an especially expedient embodiment, the cap is locked against rotation in a direction to release the coupling by a valve actuator of the female member. The female part of the coupling includes a valve for closing the connection between the hub socket and the cannula tube, e.g., when there is no male part fitted to the socket. The valve conveniently comprises a tube section with a flexible wall enabling the tube to be collapsed by a pinching action to close the passageway through the tube. An element, such as a ball, for pressing on the tube can be actuated by a slider on the female coupling member. This slider, in the preferred construction, carries the splined collar which interlocks with the sleeve fast with the cap.

In accordance with a further aspect of the invention provides a medical coupling in which the male and female members have finger gripping sections at which the members may be held to bring the spigot and hub together and to rotationally engage the securing cap with the hub. The gripping sections being axially spaced from the hub and cap, and a casing is provided to define a sealed housing around the coupled parts of the male and female members with the gripping sections remaining outside the housing.

By this construction an hermetically sealed enclosure can be formed around the parts with which fluids being administered to a patient may come into contact, and as the only parts which need to be handled are located outside the sealed enclosure, the risk of the enclosed parts becoming contaminated, such as by bacteria which can colonise on the surfaces, is significantly reduced.

In case where there is a locking device, such as the splined collar described above, this device can be located on the female member so as to be housed within the casing when it is fitted to the coupling. Furthermore, the interior of the casing can be so configured that it can only be closed around the coupling if the locking collar is in its correct locking position. This means that where the locking collar is fixed to the valve actuator, the casing can be arranged so that it can not be successfully applied with the valve in a closed condition. So that the locking collar and/or valve actuator can be adjusted without need to be touched with the hand, a tool, conveniently a two pronged fork, can be provided in a sterile pack with the casing and possibly the male and/or female coupling members. The tool may serve a dual purpose in being adapted to open the sealed casing when it is desired to access the connection between the male and female members, e.g., to connect a fresh administration set.

A more complete understanding of the invention will be gained from the following more detailed description in which reference is made to the accompanying drawings, wherein:

BRIEF DESCRIPTION OF THE DRAWINGS

FIG. 1 is a schematic axial cross-section through the male and female members of a coupling according to the invention prior to their connection;

FIG. 2 is a view similar to FIG. 1 showing the male and female members after connection, but before being locked against detachment;

DETAILED DESCRIPTION OF THE PREFERRED EMBODIMENT

Figure 3:
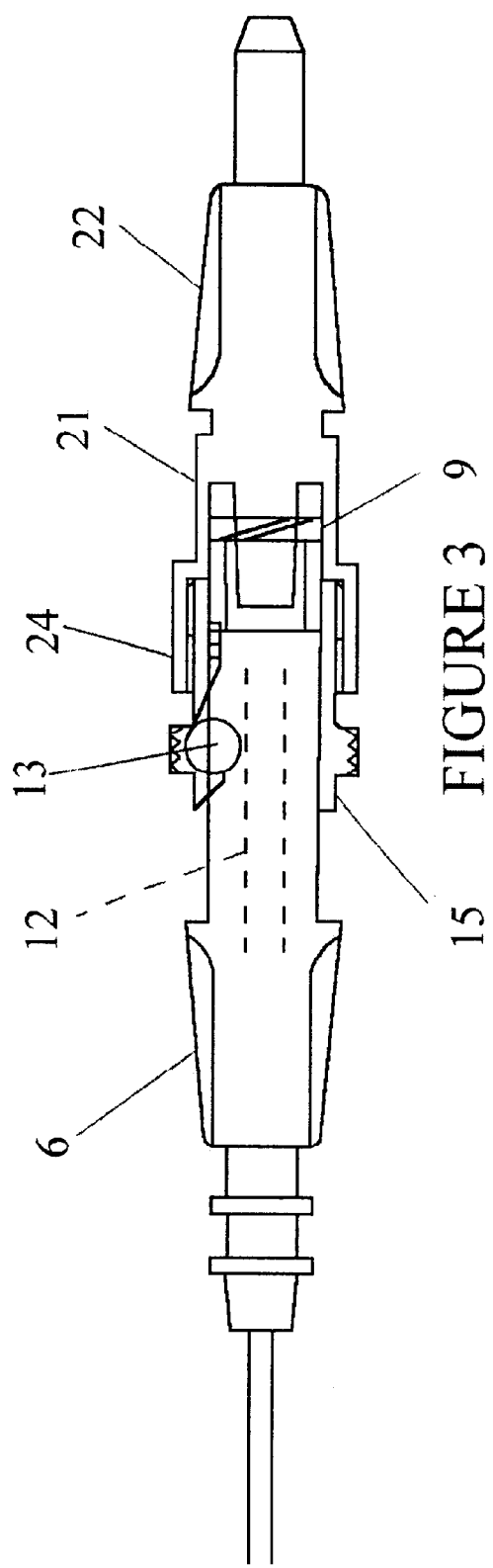
FIG. 3 shows the male and female members connected and locked together.
Figure 4:
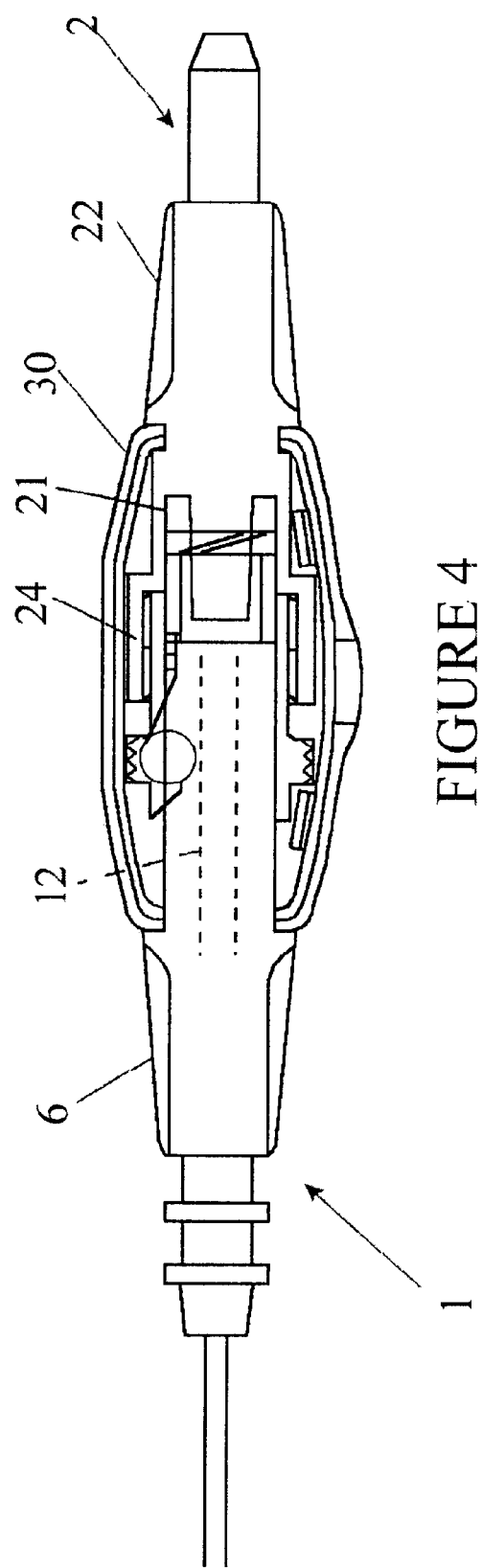
FIG. 4 shows the completed coupling with the male and female members connected and locked together and the outer casing applied.

The coupling illustrated in the drawings has a female member 1 and a male member 2. The female member is permanently attached in a sealed manner to a cannula tube 3, and includes a body defining a hub section 4, a valve section 5 and a finger gripping section 6. The finger gripping section is formed with a surface configuration, in particular longitudinal depressions 7, to facilitate firm gripping with the fingers. The hub section 4 has a flange 9 at its free end with screw thread elements 10, the purpose of which is described below. As well known per se the hub includes a frustoconical socket 11 which extends inwardly from the free end of the hub. Within the valve section 5 of the body there is accommodated a short tube 12 with a flexible wall the forward end of this tube being in communication with the cannula bore whilst the rear end of the tube is in communication with the inner end of the socket 11. A small ball 13 is received in a radial hole provided in the body, the ball being freely movable in this hole and resting on the exterior of the flexible tube 12. The ball 13 can be pressed inwardly to flatten the tube 12 and pinch closed the bore through the tube thereby interrupting communication between the cannula and the socket 11 of the hub, the tube 12 and ball 13 thus constituting a valve device. For selectively pushing the ball inwardly to close the valve, a valve actuator 15 is mounted on the body of the female member and is axially slidable thereon between a forward end position in which the valve is closed and a rear end position in which the valve is opened. The valve actuator 15 is annular and has an internal ramp surface arranged to cooperate with the ball 13. Internal projections on the valve actuator, conveniently located at the circumferential position of the ramp surface, are guided in a longitudinal slot or groove in the body and prevent free rotation of the valve actuator 15 on the body. However, a limited rotation of the valve actuator e.g. in the region of 10° to 15° is permitted for reasons which will be made clear. Extending around the valve actuator adjacent its forward end is a flange 17 which defines oppositely directed shoulders to facilitate adjustment of the valve actuator by means of a special purpose tool (not shown) having a bifurcated end the spacing between the prongs of the tool being slightly greater than the external diameter of the valve actuator either side of the flange whereby the prongs can be brought into abutment with either end face of the flange for effecting axial displacement of the valve actuator without need to touch the valve actuator. The rear end of the valve actuator has an integral collar 19 with external splines. When supplied for use the female member 1 will be in the condition shown in FIG. 1, i.e., the valve being closed.

The male member 2 can be formed essentially as a one piece moulding. It has a spigot 20 which is shaped and dimension to provide a friction sealing fit within the hub socket 11. Extending about the spigot is a cap 21 having an internal screw thread for cooperation with the threaded flange 9 of the hub 4 for securing the spigot 20 against being pulled out of the hub. Behind the cap and spigot is a finger gripping section 22 by means of which the male member 2 can be grasped in the fingers during connection of the male member to the female member of the coupling, and during their subsequent disconnection. The finger gripping section 22 is provided with depressions 7 to facilitate gripping like the gripping section of the female member. Between the finger gripping section 22 and the cap 21 is a circumferential groove for cooperation with an outer case as explained below. Integral with the forward end of the cap is a sleeve 24 with internal axial splines, e.g. in the order of 15 to 20 in number. The splined sleeve is adapted to cooperate with the splined collar 19 of the valve actuator 15 to lock the cap 21 against rotation relative to the female member of the coupling and hence prevent unintentional unscrewing of the cap 21 and disconnection of the coupling. An axial bore through the male member extends from the spigot 20 to a rear connection piece 25 by means of which the member 2 is fixedly and sealingly attached to a tube. e.g. a delivery tube of an administration set.

Holding the male and female members 1,2 by their respective finger gripping sections, the members are brought axially together so that the spigot 20 enters the hub socket 11. The members 1,2 are then relatively rotated to screw the cap 21 onto the hub flange 9 and to ensure that the spigot 20 is firmly and sealingly engaged in the hub socket 11, this being the condition shown in FIG. 2. By means of the tool described above, the valve actuator 15 is slid rearwardly along the body of the female member so that the splined collar 19 enters the splined sleeve 24. If the splines of the collar are not in precise alignment with the grooves between the splines of the sleeve, a small amount of rotation of the valve actuator will provide the necessary alignment. The leading ends of the splines on the collar 19 and the sleeve 24 are shaped to ensure a smooth and reliable engagement of the collar into the sleeve and to bring about automatically any rotation of the collar necessary to align the splines of the collar with the grooves defined between the splines of the sleeve. More particularly, the spline ends are chamfered and their lateral faces are tapered in a V-shape so that the confronting spline ends will be brought together gradually and will produce a camming action to rotate the valve actuator as necessary to obtain the rotational alignment necessary for the collar 19 to engage fully within the sleeve.

When the collar 19 is correctly engaged in the sleeve 24, as shown in, FIG. 3, the cap 21 is locked against rotation and the valve is opened, the tube 12 expanding under its own resilience when the ball l; is permitted to mare radially outwardly to the ramp surface of the valve actuator. The coupling and locking of the male and female members is achieved without any parts of the two members other than the gripping sections 6,22 being touched with the hands.

Figure 6:
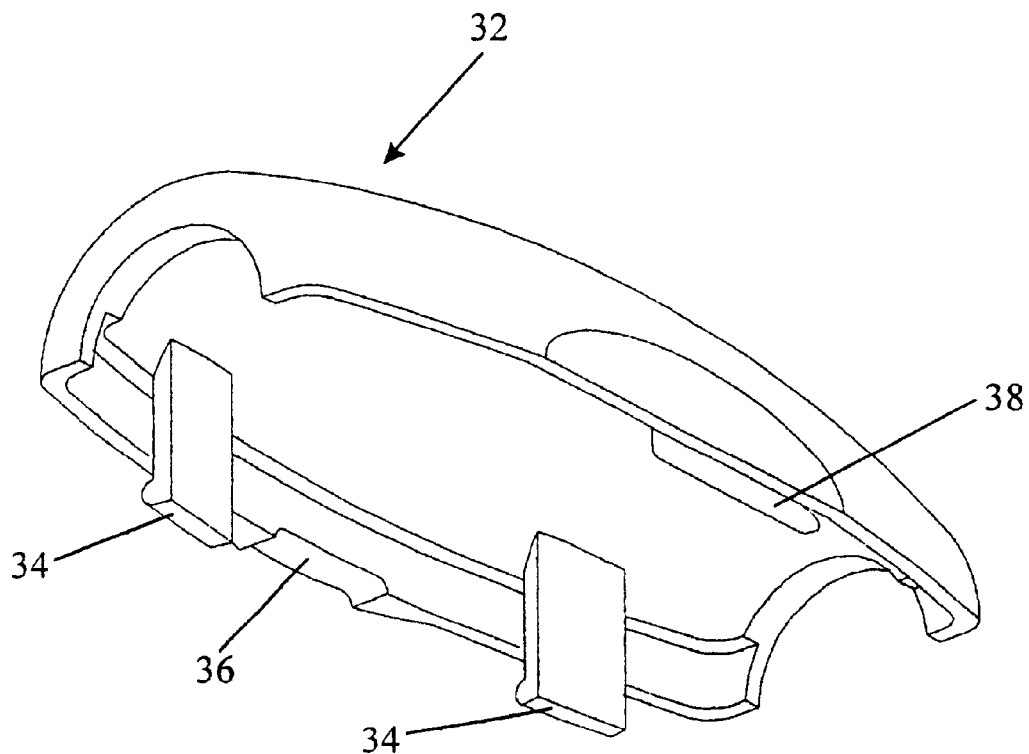
FIGS. 5 and 6 are isometric views of the two halves of the shell of the casing.
Figure 5:
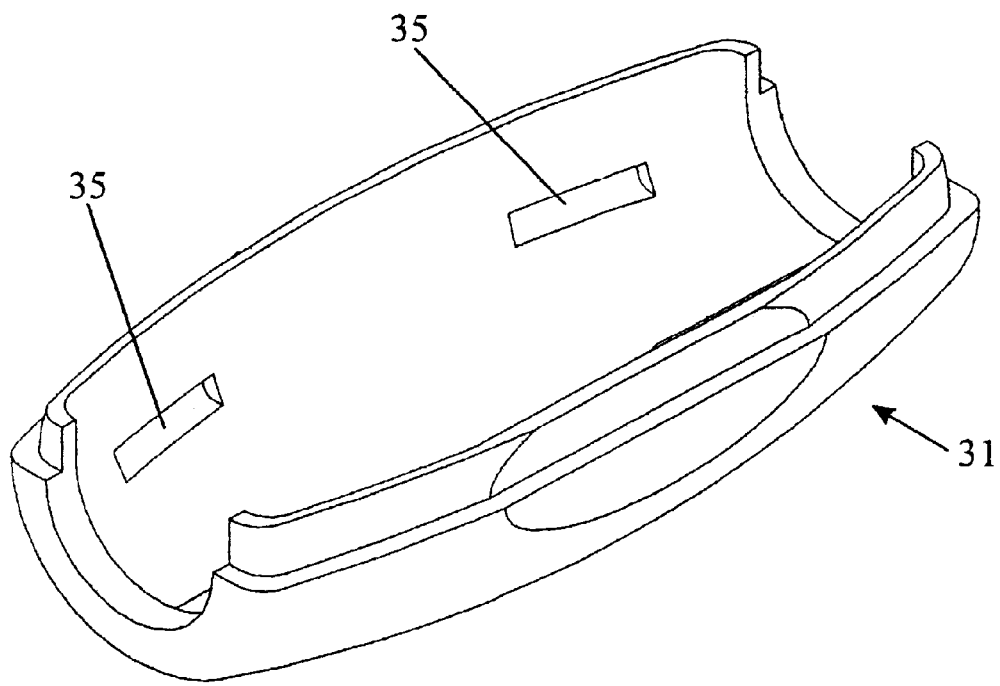

For additional security against disconnection and infection an outer casing 30 is applied over the coupling between the finger gripping sections. The case, as shown in FIGS. 5 and 6, includes two parts 31,32 which may be separate as illustrated, but are preferably connected by an integral hinge along one edge, namely the right hand edge as viewed in the drawings. For locking the two casing parts together in the closed condition integral latch fingers 34 are provided in one part and have a snap engagement in slots 35 provided in the inner surface of the other part. The casing parts have stepped edges to improve the seal obtained when the parts are closed together around the coupled male and female members. A notch 36 is defined between the externally confronting edge faces, and the same tool as used for adjusting the valve actuator 15 may be inserted in this notch and twisted for opening the casing to gain access to the coupling to enable it to be disconnected if required. It may be desirable to arrange for the casing 30 to be rendered unserviceable., such as by the latch fingers becoming fractured on opening of the casing so that it becomes necessary to use a fresh sterile case. When the casing has been opened the valve actuator 15 can be slid forwardly, against using the tool previously described, thereby closing the valve and unlocking the cap 21 so that the male and female members may be uncoupled, if required by holding and relatively rotating the gripping sections 6,22 to release the cap 21.

It will be noted that the casing 30 has inwardly directed rims at its ends, these rims being arranged so that they fit tightly around the two coupling members 1,2 adjacent but between the finger gripping sections 6,22 which remain outside the casing so that risk of contamination of the parts within the casing interior is minimised. Also, the interior of the casing has protrusions 38 so positioned that if attempt is made to fit the casing with the coupling unlocked and the valve closed the protrusions will encounter the flange 17 of the valve actuator and it will not be possible to close the casing sufficiently to engage the latch fingers 3,4

From the foregoing it will be appreciated that the invention provides a very secure coupling which if used as intended carries reduced risk of contamination of those parts at which the fluid connection is effected.

What is claimed is:

1. A coupling for a medical cannula or the like comprising a female member (1) having a socket (11), a male member (2) having a spigot (20) engagable with a push fit into the socket (11), a cap (21) attached to one member and rotationally engagable with the other member to secure the spigot against disengagement from the socket, and a locking engagement to lock the cap (21) against rotation in the direction of disengagement from said other member, wherein the locking arrangement comprises a sleeve (24) provided on the cap and a slide (19) movably mounted on said other member, the slide (19) being movable on the other member after the spigot has been secured against disengagement from the socket (11) by rotational engagement of the cap (21) with the other member so as to engage the slide (19) with the sleeve and thereby lock the sleeve and cap against rotation in a disengagement direction.

2. A coupling according to claim 1, wherein the slide (19) and sleeve (24) are engageable through a splined connection.

3. A coupling according to claim 2 wherein the sleeve (24) is internally splined.

4. A coupling according to claim 2, wherein the slide (19) is externally splined.

5. A coupling according to claim 2, wherein the spline connection includes splines on the sleeve and splines on the slide, and the slide (19) is capable of rotation relative to the other member through a limited angle substantially less than a full revolution for bringing the splines on the slide and on the sleeve into alignment during engagement of the slide (19) with the sleeve (24).

6. A coupling according to claim 5, wherein the ends of the splines are shaped to bring about automatically any rotation of the slide (19) necessary to allow locking engagement of the slide (19) with the sleeve (24).

7. A coupling according to claim 1, wherein the slide comprises a splined collar (19).

8. A coupling according to claim 1, wherein the cap (21) and sleeve (24) are provided on the male member (2) and the slide (19) is movably mounted on the female member (1).

9. A coupling according to claim 8, wherein the female member includes a valve having a valve actuator (15), the slide (19) being movable with the valve actuator.

10. A coupling according to claim 9, wherein axial movement of the valve actuator (15) to open the valve brings the slide (19) into engagement with the sleeve.

11. A coupling according to claim 9 wherein the valve comprises a flexible-walled tube (12) within a body of the female member, and an element (13) movable radially by the actuator (15) to close the tube with a pinching action.

12. A coupling according to claim 9, wherein a separate tool is provided for moving the valve actuator to open the valve without the actuator being touched by hand.

13. A coupling according to claim 1, wherein the male and female members (1,2) have finger gripping sections (6,22) at which the members are intended to be held during engagement of the spigot (20) in the socket (11) and engagement of the cap, and a casing (30) is provided to define a sealed housing around the coupled parts of the male and female members with the gripping sections (6,22) remaining outside the housing.

14. A coupling for a medical cannula or the like comprising a female member (1) having a socket (11), and a male member (2) having a spigot engageable with a push fit into the socket (11), a cap (21) attached to one member and rotationally engageable with the other member to secure the spigot against disengagement from the socket, wherein the male and female members have finger gripping sections (6,22) at which the members are intended to be held during engagement of the spigot in the socket and engagement for the securing cap (12), and a casing is provided to define a sealed housing around the socket, spigot and cap of the male and female members when coupled together, with the gripping sections (6,22) remaining outside the housing.

15. A coupling according to claim 14, wherein the casing comprises two parts (31,32) having cooperable snap engagement means (34,35) to secure the casing parts together in a closed condition.

16. A coupling according to claim 15, wherein the casing parts are connected together by an integral hinge.

17. A coupling according to claim 15, wherein the snap engagement means are arranged to fracture upon opening the closed case to prevent re-use of the case.

18. A coupling according to claim 15, wherein the casing parts have stepped edges at which the parts sealingly engage when the casing is closed.

19. A coupling according to claim 14, wherein the female member includes a valve with a movable actuator, and the casing has abutment means (38) of the interior thereof to prevent the casing being closed with the valve in a closed condition.

20. A coupling according to claim 14, wherein the casing has rims directed inwardly at the ends thereof for tightly engaging the male and female members (1,2) adjacent but between the gripping sections (6,22).

* * * * *